United States Patent
Chuang et al.

(10) Patent No.: US 8,367,018 B2
(45) Date of Patent: Feb. 5, 2013

(54) CHIP WITH TRI-LAYER ELECTRODE AND MICRO-CAVITY ARRAYS FOR CONTROL OF BIOPARTICLE AND MANUFACTURING METHOD THEREOF

(75) Inventors: Cheng-Hsin Chuang, Yung-Kung (TW); You-Ming Hsu, Yung-Kung (TW); Yao-Tung Wu, Yung-Kung (TW)

(73) Assignee: Southern Taiwan University of Technology, Tainan County (TW)

( * ) Notice: Subject to any disclaimer, the term of this patent is extended or adjusted under 35 U.S.C. 154(b) by 105 days.

(21) Appl. No.: 12/591,966

(22) Filed: Dec. 7, 2009

(65) Prior Publication Data

US 2011/0136698 A1    Jun. 9, 2011

(51) Int. Cl.
*B01L 3/00* (2006.01)

(52) U.S. Cl. ........ 422/502; 422/503; 422/504; 422/547; 422/551; 422/552

(58) Field of Classification Search .............. 204/403.01, 204/450; 435/287.1, 288.2; 422/547, 551, 422/552, 502, 503, 504
See application file for complete search history.

(56) References Cited

U.S. PATENT DOCUMENTS

| | | | | |
|---|---|---|---|---|
| 5,506,141 A | * | 4/1996 | Weinreb et al. | 435/309.1 |
| 6,692,952 B1 | * | 2/2004 | Braff et al. | 435/288.4 |
| 6,773,566 B2 | * | 8/2004 | Shenderov | 204/450 |
| 6,932,893 B2 | * | 8/2005 | Bech et al. | 204/403.01 |
| 6,989,089 B2 | * | 1/2006 | Nisch et al. | 205/777.5 |

* cited by examiner

*Primary Examiner* — Jill Warden
*Assistant Examiner* — Dwayne K Handy
(74) *Attorney, Agent, or Firm* — Rosenberg, Klein & Lee

(57) ABSTRACT

A chip with tri-layer electrodes and micro-cavity arrays for control of bioparticles and a manufacturing method thereof are revealed. The chip captures and releases bioparticles into and from preset cavities by dielectrophoresis (DEP) force generated by electrodes. The chip includes an upper layer body, a middle layer body, a lower layer body, respectively disposed with an electrode, and micro flow chambers. The electrodes of the upper layer body and the middle layer body are common electrodes while the electrode of the lower layer body is a dispersive electrode array exposed on the bottom of lower-layer microcavity. The cell capture and release at the single-cell level and the cell population level are attained by application of an AC electric field.

4 Claims, 13 Drawing Sheets

CHIP WITH TRI-LAYER ELECTRODE AND MICRO-CAVITY ARRAYS FOR CONTROL OF BIOPARTICLE AND MANUFACTURING METHOD THEREOF

BACKGROUND OF THE INVENTION

1. Fields of the Invention

The present invention relates to a chip with tri-layer electrodes and micro-cavity arrays for control of bioparticles and a manufacturing method thereof, especially to a chip that captures and releases cells/bioparticles into/from preset cavities by dielectrophoresis (DEP) force generated by electrodes, and a manufacturing method thereof. Cell trapping, cell release at the single-cell level and cell release at the cell population level are achieved by combinations of tri-layer electrodes and applications of AC (alternating current) electric field.

2. Descriptions of Related Art

Due to well development of MEMS (Micro Electro Mechanical Systems), studies regarding manipulation of a single cell have achieved great development. Among these studies, applications of dielectrophoresis force on biochips for cell positioning are most popular. The modules of cell biochips with the applications of dielectrophoresis have following functions: cell immobilization, transmission, separation, measurement, cell sorting, etc.

Publications on dielectrophoresis go as far back as 1978, by Herbert Pohl, England. Dielectrophoresis is defined as a phenomenon that when a cell is subjected to a non-uniform electric field such as non-uniform AC (alternating current) electric field, the cell surface is with induced charge due to dielectric property of the cell and a dipole moment with the same or opposite direction of the applied electric field is formed. Thus the cell is attracted to regions of stronger electric field due to positive dielectrophoresis force or concentrated to regions of weaker electric field by negative dielectrophoresis force. Therefore the electrode design allows the cell to be driven by the electric field gradient and fixed in a designed (preset) area.

Traditional techniques are divided into several groups as followings:
1. Refer to Taiwanese Pub. App. No. 1308131 (Prior art I), a bioparticle capture apparatus with three-dimensional microstructure is revealed, as shown in FIG. 12. The three-dimensional microstructure includes an upper layer, a lower layer and micro flow channels. The upper layer and the lower layer are respectively disposed with electrodes so as to generate dielectrophoresis (DEP) force for capturing bioparticles into preset wells. Except capture of bioparticles by DEP force, there is no other manipulation way of cells. The function of the device is limited.
2. Refer to U.S. Pat. No. 6,692,952 (Prior art II), as shown from FIG. 13a to FIG. 13d, a cell analysis and sorting apparatus is revealed. The apparatus contains several cell locations (wells) that capture, hold and release the cells. An electric field trap formed by electrodes is used for capturing the cell and vapor bubbles eject the cell out of the well. The apparatus can also use to observe cell behavior, and sort cells.
The electrodes are formed from gold and gaskets are made from PDMS (poly dimethyl siloxane). By applying current to electrodes, an electric field is produced to trap cells. After analysis, the vapor bubbles cause cell release. However, the longer the cell contacts with electrode, the greater the number of cell dead. Moreover, production of vapor bubbles may require higher or lower voltage/frequency. These conditions are not suitable for cell studies.

Among related studies, there is no single chip that attains both cell capture and programmable cell release at the single-cell level. Thus there is a need to develop a chip and a manufacturing method thereof that overcomes shortcomings of the techniques and chips available now and has more practical value.

SUMMARY OF THE INVENTION

Therefore it is a primary object of the present invention to provide a chip with tri-layer electrodes and micro-cavity arrays for control of bioparticles that achieves purposes of cell trapping, cell release at the single-cell level and cell release at the cell population level.

In order to achieve above object, the chip includes an upper layer body, a middle layer body, a lower layer body, and micro flow chambers. The upper layer body, the middle layer body, and the lower layer body are respectively disposed with an electrode. The electrodes of the upper layer body and the middle layer body are common electrodes while the electrode of the lower layer body is a dispersive electrode array exposed on the bottom of lower-layer microcavity. The cell capture and release are attained by application of an AC electric field.

It is another method to provide a manufacturing method of chips with tri-layer electrodes and micro-cavity arrays for control of bioparticles so as to position bioparticles and manipulate cells.

In order to achieve object, the method includes following steps. A specimen formed by a glass substrate coated with a layer of metal such as gold is coated with a photoresist and then is undergone an exposure. Then the exposed specimen is immersed into a developer for development and is soaked into an etching solution to produce a lower-layer electrode. Next coat the lower-layer electrode of the specimen with photoresist and perform an exposure. The exposed specimen is immersed into a developer for development and then a step of hard bake is performed to construct microcavities. Later coat photoresist on the microcavities and run an exposure. The exposed specimen is soaked into a developer for development and then is coated with a layer of gold by evaporation. Then the photoresist is removed by a lift-off process and the middle-layer electrode is produced. At last, connect the middle-layer electrode with an upper-layer electrode, a chip for control of cells is finished.

After completing production of the chip, the finished chips are connected with wires and signal generators so as to be applied to cell manipulation experiments.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein:

FIG. 11A is a schematic drawing showing a bioparticle on a chip when an electric field is formed;

FIG. 11B is a schematic drawing showing a bioparticle on a chip when an upper-layer electrode and a middle-layer electrode both work;

FIG. 11C is a schematic drawing showing a bioparticle on a chip when signal generators of an upper-layer electrode and of a middle-layer electrode are turned off and then the upper-layer electrode and the middle-layer electrode are turned on;

DETAILED DESCRIPTION OF THE PREFERRED EMBODIMENT

Figure 1:
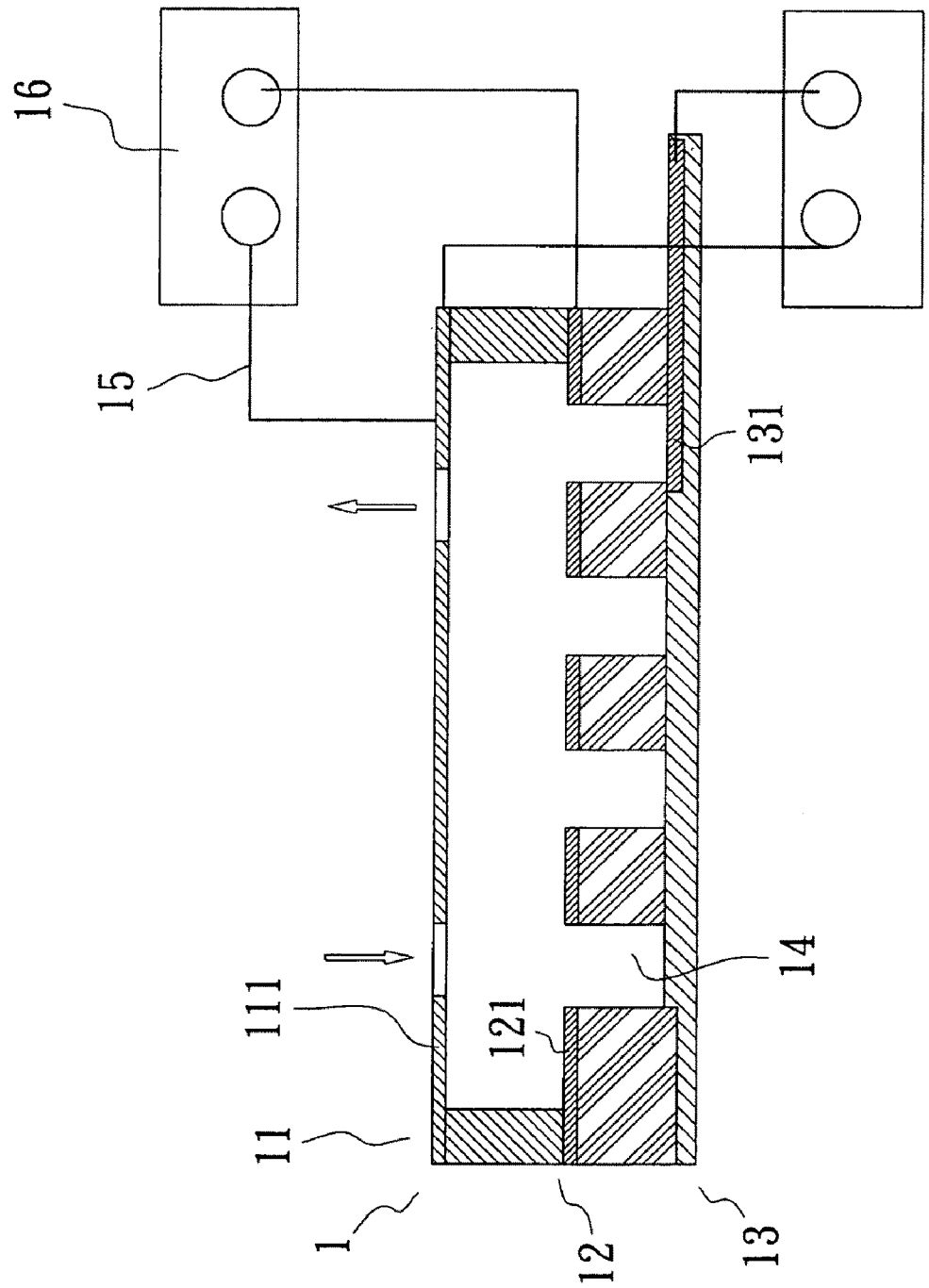
FIG. 1 is a schematic drawing showing structure of an embodiment of a chip according to the present invention.
Figure 2:
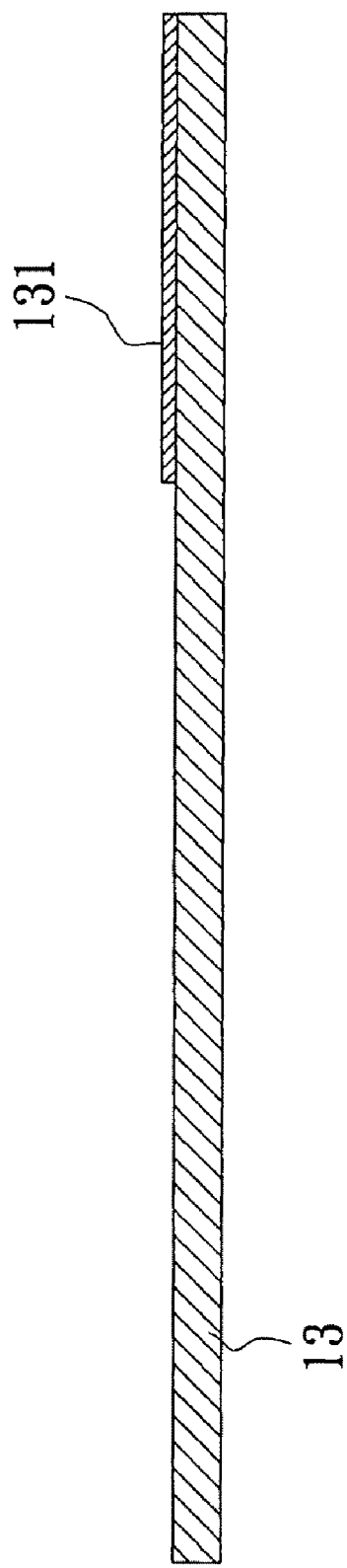
FIG. 2 is a schematic drawing showing a flow chart of a manufacturing method of the chip according to the present invention.
Figure 3:
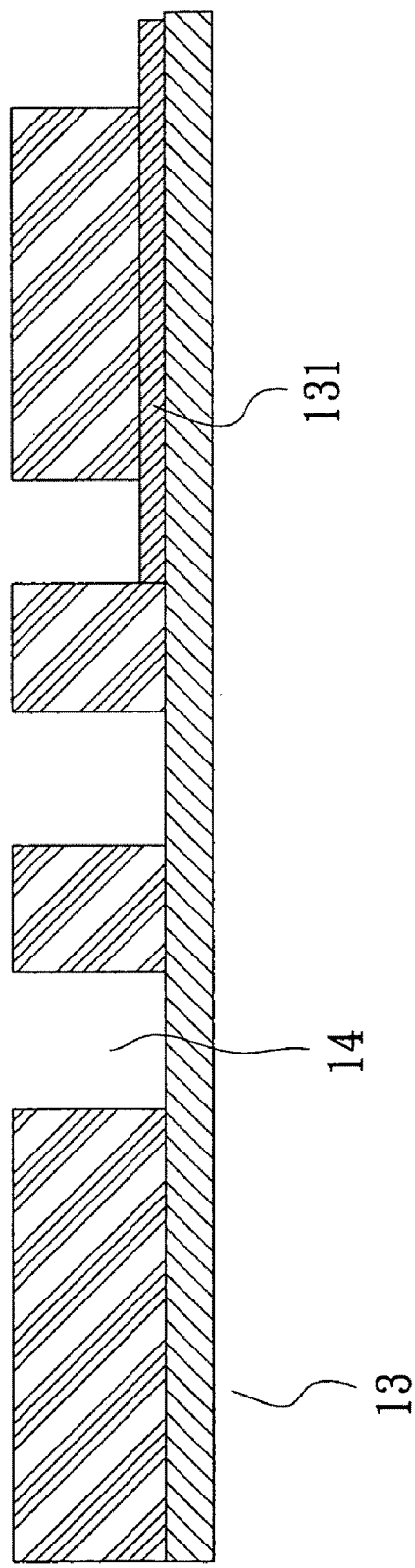
FIG. 3 is another schematic drawing showing a flow chart of a manufacturing method of the chip according to the present invention.
Figure 4:
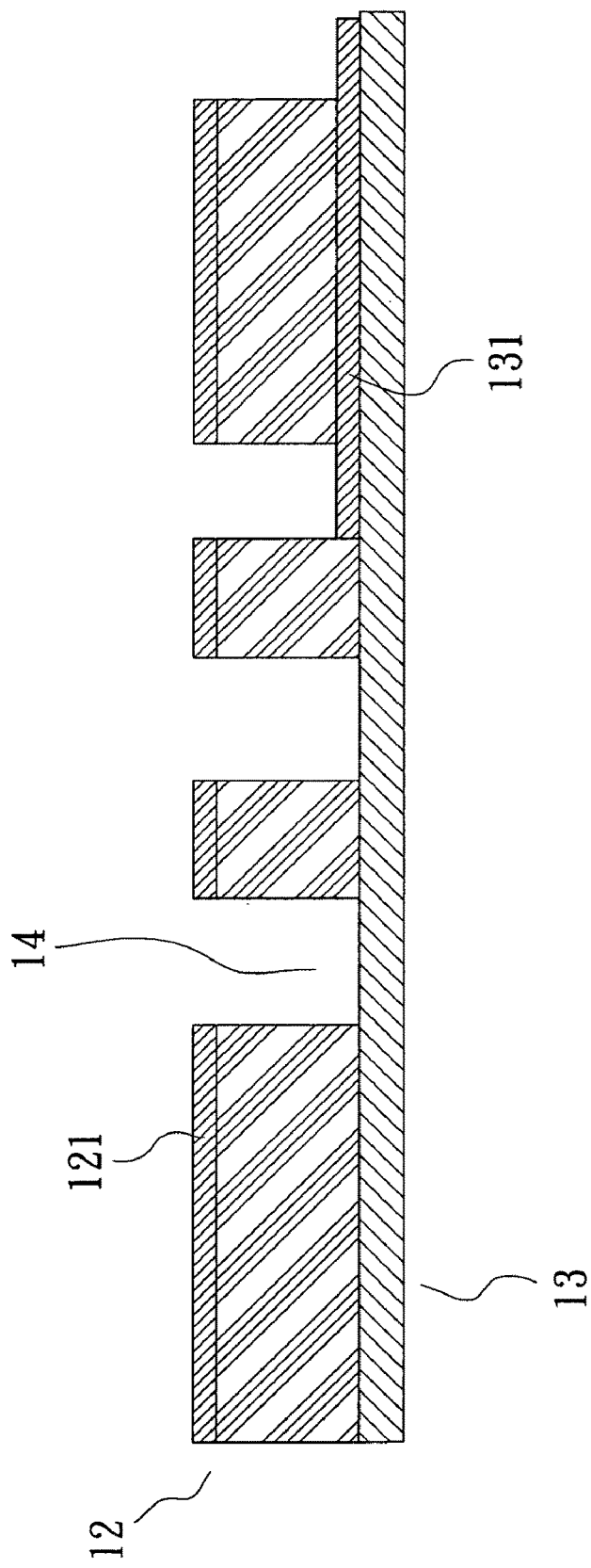
FIG. 4 is a further schematic drawing showing a flow chart of a manufacturing method of the chip according to the present invention.
Figure 5:
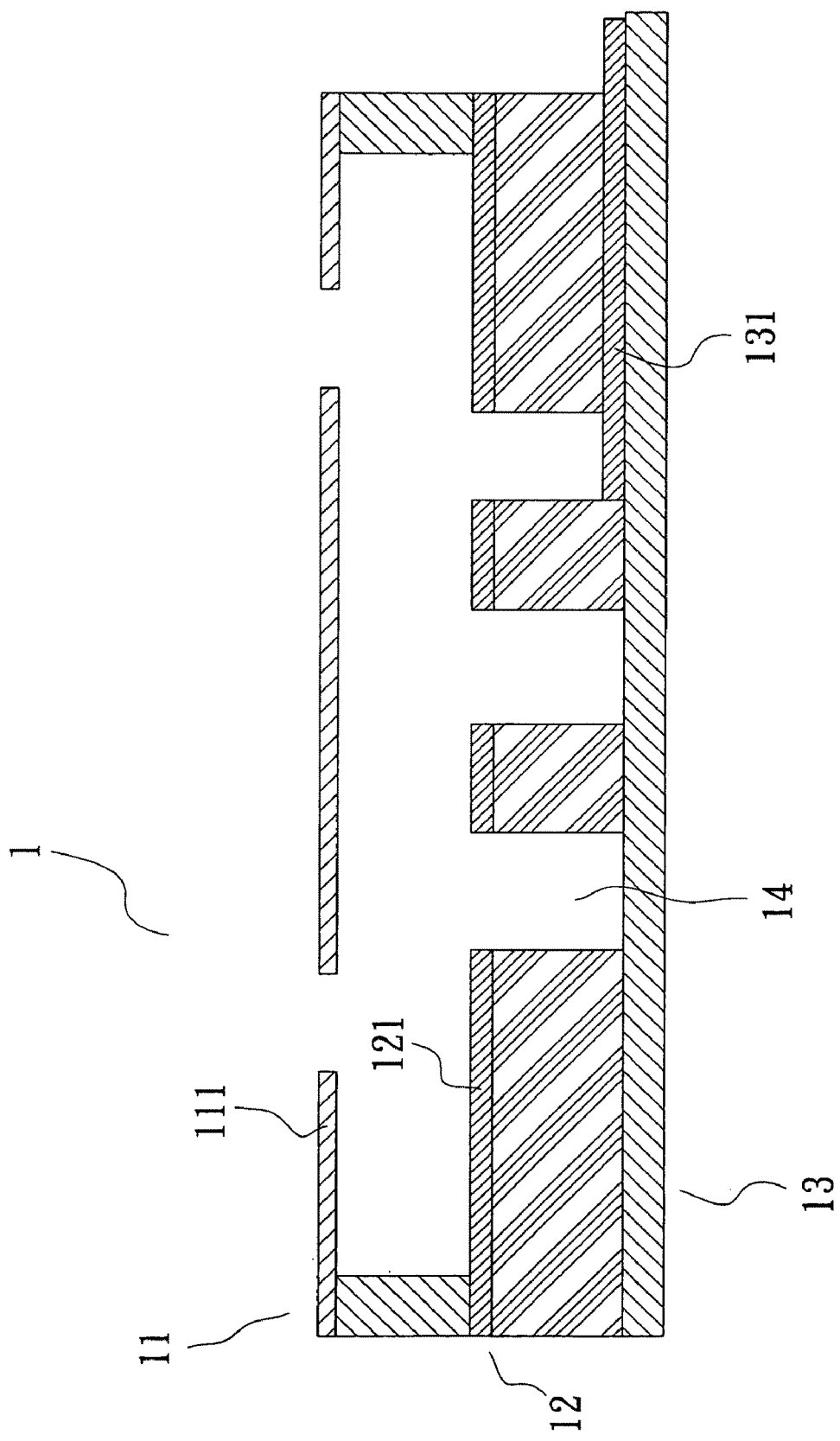
FIG. 5 is a further schematic drawing showing a flow chart of a manufacturing method of the chip according to the present invention.

Refer to FIG. 1 a schematic drawing showing structure of a chip with tri-layer electrodes and micro-cavity arrays for control of bioparticles 1 includes an upper layer body 11, a middle layer body 12, a lower layer body 13, and micro flow chambers. The upper layer body 11, the middle layer body 12, and the lower layer body 13 are respectively disposed with an electrode 111, 121, 131. The electrodes of the upper layer body 11 and the middle layer body 12 are common electrodes 111, 121 while the electrode 131 of the lower layer body 13 is a dispersive electrode array exposed on the bottom of lower-layer microcavity 14. By combinations of the tri-layer electrodes and application of an AC electric field, trapping of cells, and release of cells at the single-cell level or at the cell population level can be achieved.

Cell trapping: make directions of the electric fields of the upper layer body 11 and the middle layer body 12 become perpendicular to the direction of flow field of micro flow chambers to form a non-uniform electric field along lengthwise direction. Thus bioparticle floating and flowing in the micro flow chambers are trapped into the microcavity 14 arranged at the lower layer body 13 efficiently. The microcavity 14 not only improves trapping efficiency and resolution but also avoids shortcomings of overlapping and aggregation so as to achieve trapping at the single-cell level or the single-particle level. Moreover, after absorption, the cell is fixed by vacuum adsorption of the cavity and lateral support of the microstructure and there is no need to keep providing an AC power required to generate the dielectrophoresis force. Thus cell viability on the chip is dramatically increased.

Cell release at the single-cell level: cell release at a preset position is achieved effectively by a vertical non-uniform electric field formed by the common electrode 111 of the upper layer body 11 and the dispersive electrode 131 of the lower layer body 13.

Cell release at the cell-population level: all cells in the microcavity 14 are released by a vertical non-uniform electric field formed by the common electrodes 111, 121 of the upper layer body 11 and the middle layer body 12.

Moreover, refer from FIG. 1 to FIG. 5, a manufacturing method for chips with tri-layer electrodes and micro-cavity arrays for control of bioparticles includes the following steps.

1. etch a lower-layer electrode: a glass substrate is coated with a layer of metal such as gold by evaporation to form a specimen that is then coated with a photoresist and undergone an exposure. The exposed specimen is immersed into a developer for development and is soaked into an etching solution to finish the production of the lower-layer electrode 131.

2. construct microcavities: coat the lower-layer electrode 131 of the specimen with photoresist and perform an exposure. The exposed specimen is immersed into a developer for development and then a step of hard bake is performed. The construction of microcavities 14 is completed.

3. produce a middle-layer electrode: again coat photoresist on the microcavities 14 and run an exposure. The exposed specimen is soaked into a developer for development and then is coated with a layer of metal (gold) by evaporation. Then the photoresist is removed by a lift-off process and the middle-layer electrode 121 is produced.

4. Assemble final products: after connecting the middle-layer electrode 121 with an upper-layer electrode 111, a chip for control of cells 1 is finished.

After finishing above steps, the chip for control of cells 1 is connected with wires 15 and signal generators 16 to be used for cell manipulation experiments.

Figure 6:
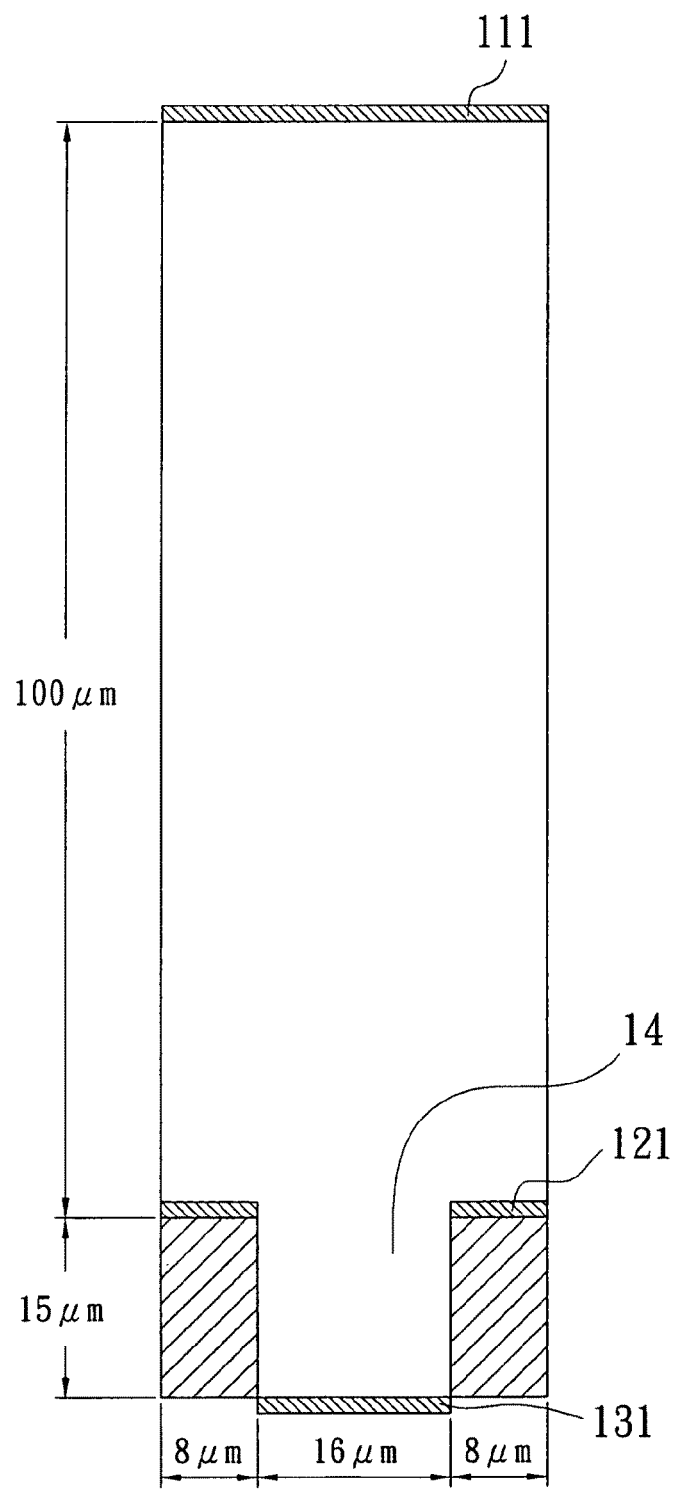
FIG. 6 is a schematic drawing showing a simulation result of an embodiment according to the present invention.

Refer to FIG. 6, a computer simulation of a chip for manipulation cells according to the present invention is revealed.

Firstly, a 2D model to be simulated is obtained by CFD-GEOM software and then grids are generated. The conditions set is: the total height is 115 μm, the height of the photoresist SU-8 is 15 μm, the height of the chamber is 100 μm. The interval of the photoresist SU-8 is 8 μm and the diameter of the microcavity is set as 16 μm.

The established modeling is saved and then set simulation parameter by CFD-ACE. The parameters set by CFD-ACE include electric field frequency, materials, boundary conditions, input voltage, the number of simulation steps, etc. After simulation, the simulated electric field strength and the gradient of the electric field square are read by CFD-VIEW.

Figure 7:
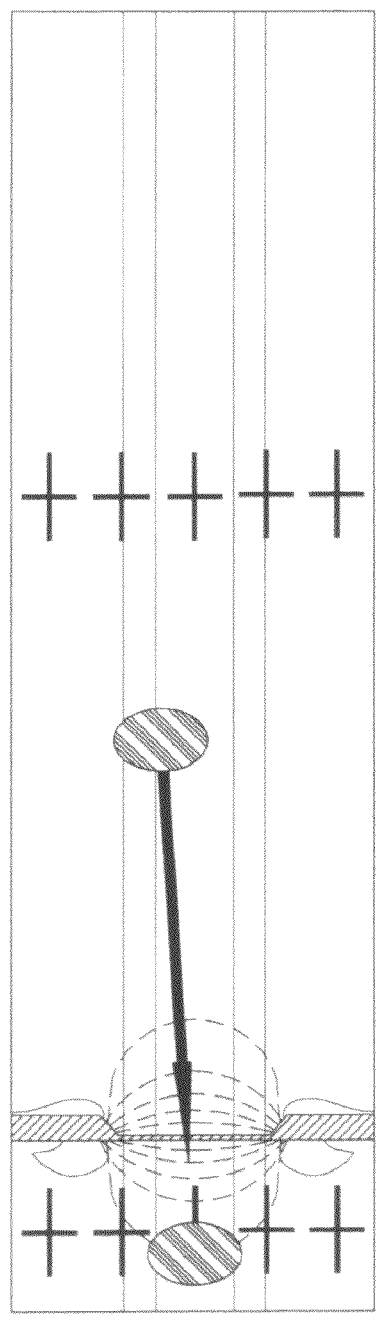
FIG. 7 is a computer simulation showing electric field distribution of an embodiment according to the present invention.
Figure 8:
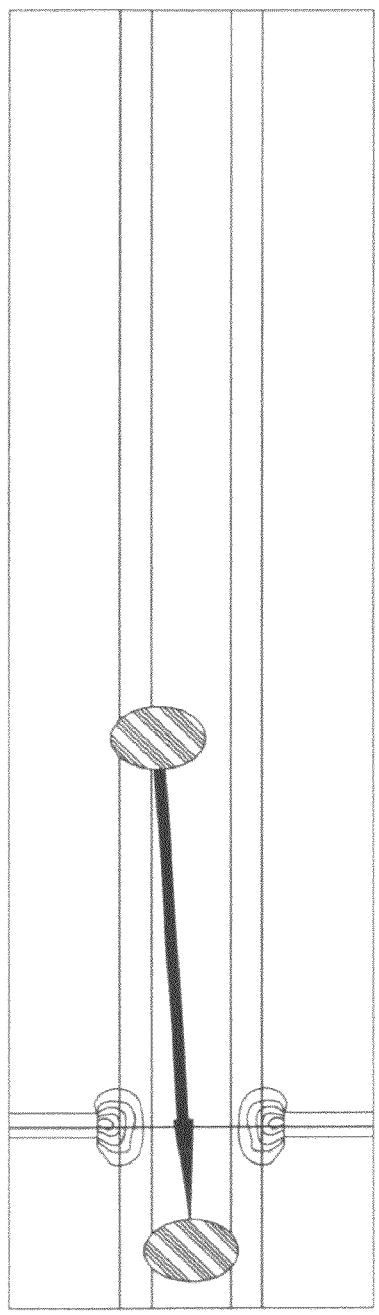
FIG. 8 is a computer simulation showing gradient of the electric field square of an embodiment according to the present invention.
Figure 11:
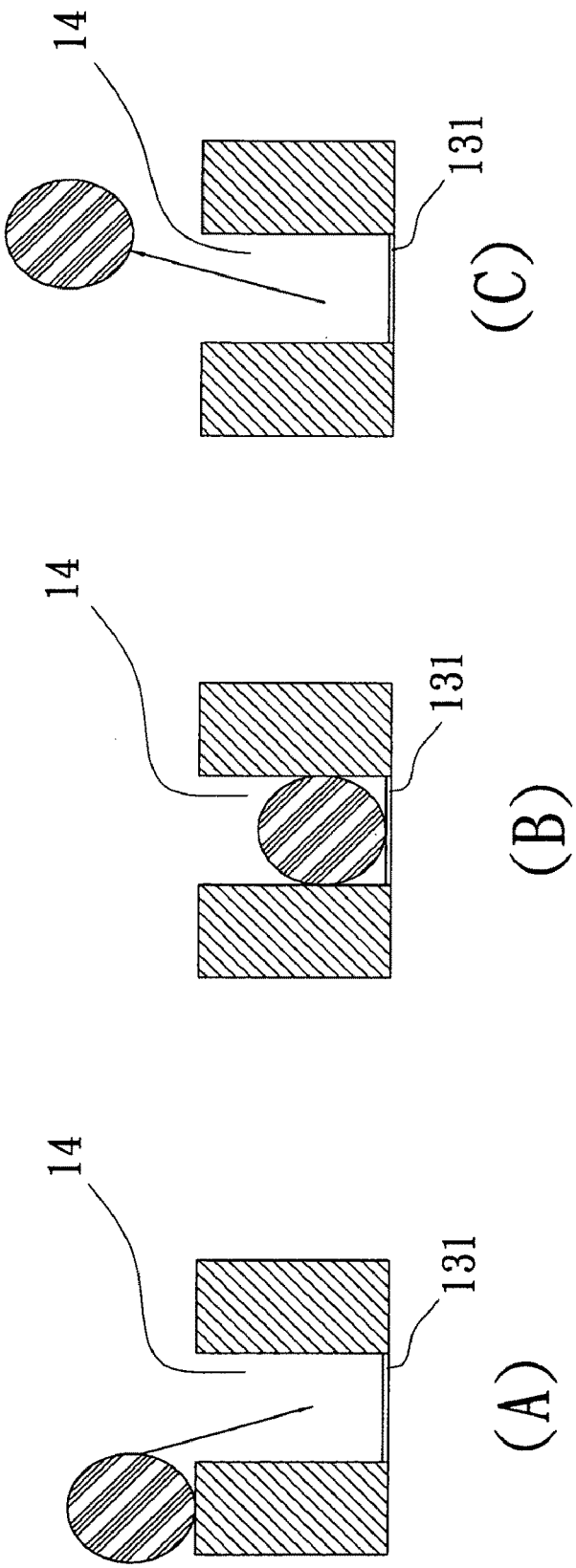
Figure 12:
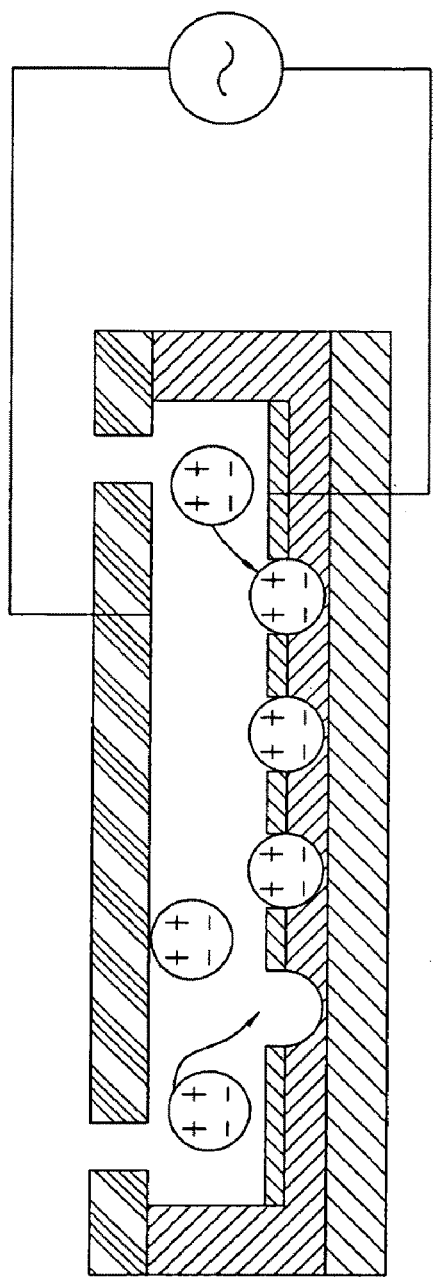
FIG. 12 is a schematic drawing of an embodiment of a prior art.
Figure 13:
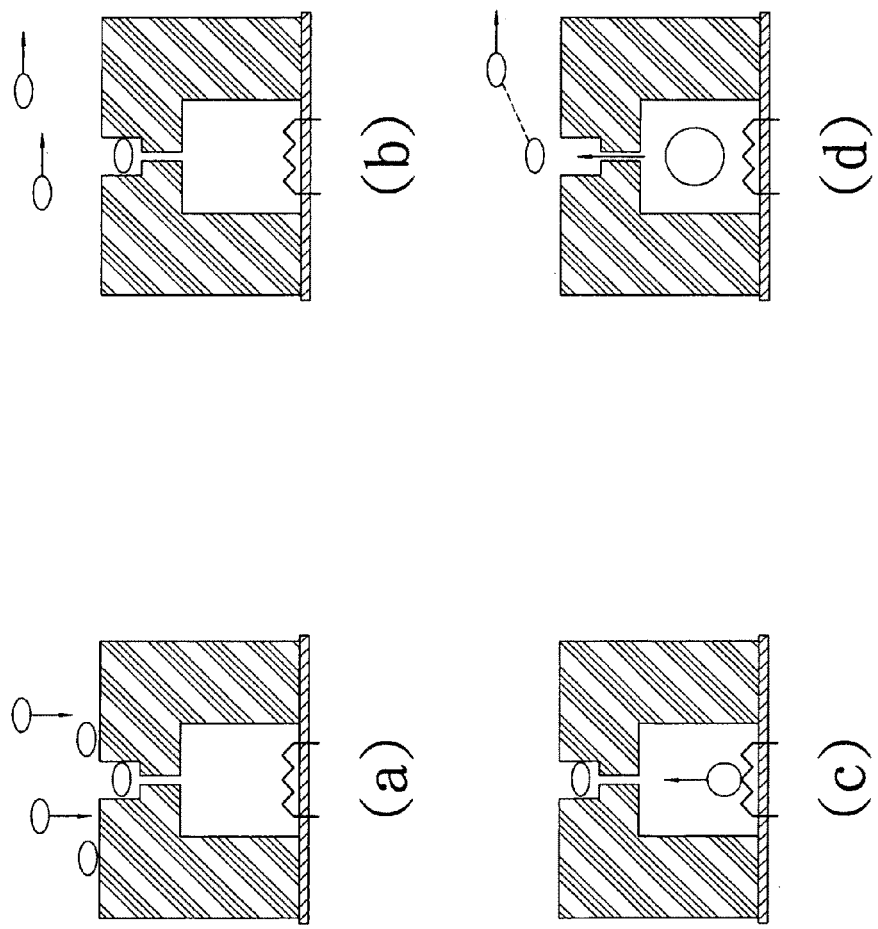
FIG. 13a to FIG. 13d are schematic drawings of another embodiment of a prior art.

Refer to FIG. 7, FIG. 8 and FIG. 11, the conditions of the simulation are set as followings: the input voltage of the upper-layer electrode is 0V and the input voltage of the middle-layer electrode is 10 V (Volts). FIG. 7 is a simulated electric field distribution while FIG. 8 shows simulated gradient of the electric field square. Refer to FIG. 7, by the electric field distribution, it is checked that cells or particles are under influence of the lengthwise non-uniform electric field formed by the electric fields of electrodes 111, 121 on the upper layer body 11 and the middle layer body 12, and the flow field of micro flow chambers while the direction of the electric field and the direction of the flow field are perpendicular to each other. Thus cells or bioparticles floating and flowing in the micro flow chambers are trapped into the microcavity 14 arranged at the lower layer body 13 quickly and efficiently. The same principle can explain that the value magnitude of the gradient of the electric field square of electrodes 111, 121 on the upper layer body 11 and the middle layer body 12 also has effects on capturing of cells/bioparticles into the microcavity 14 arranged at the lower layer body 13.

Figure 9:
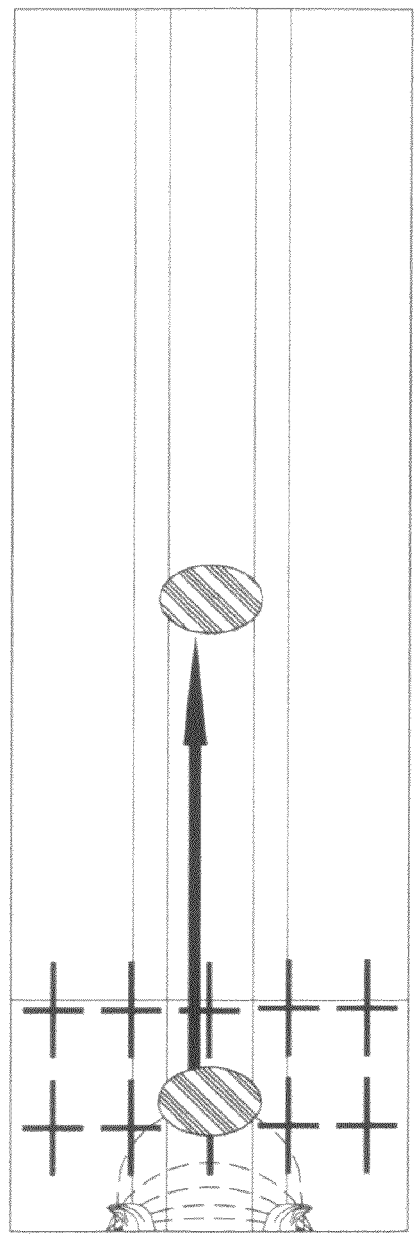
FIG. 9 is a computer simulation showing electric field distribution of another embodiment according to the present invention.
Figure 10:
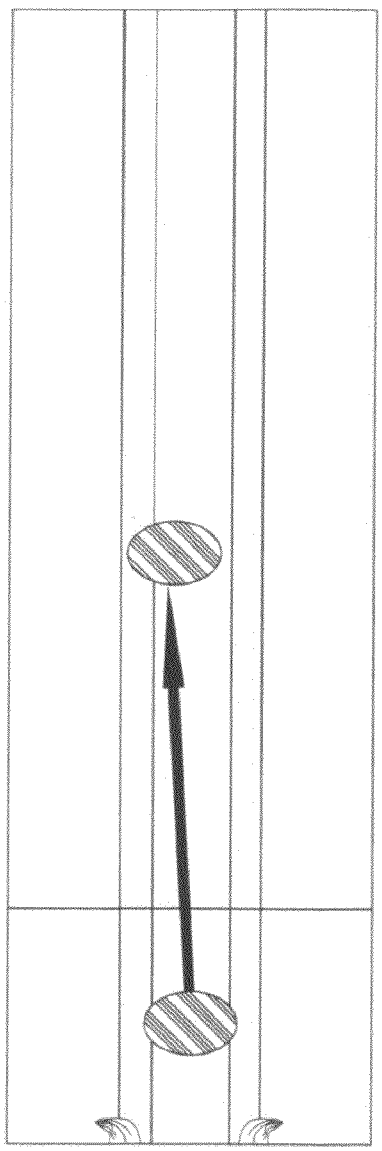
FIG. 10 is a computer simulation showing gradient of the electric field square of another embodiment according to the present invention.

Refer from FIG. 9 to FIG. 10, the conditions of the simulation are set as followings: the input voltage of the upper-layer electrode is 0V and the input voltage of the lower-layer electrode is 10 V (Volts). FIG. 9 is a simulated electric field distribution while FIG. 10 shows simulated gradient of the electric field square. As the electric field distribution shows in FIG. 9, it is checked that cells or particles are under influence of the lengthwise non-uniform electric field formed by the electric fields of electrodes 111, 131 on the upper layer body 11 and the lower layer body 13, and the flow field of micro flow chambers while the direction of the electric field and the direction of the flow field are perpendicular to each other. Thus cells or bioparticles are released from the microcavity 14 to the micro flow chambers efficiently. The same principle can explain that the value magnitude of the gradient of the electric field square of electrodes 111, 131 on the upper layer body 11 and the lower layer body 13 also has effects on releasing of cells/bioparticles into the micro flow chambers.

In summary, the present invention has following advantages compared with structures available now:

1. Compared with the prior art I whose function is mainly related to cell capture, the present invention traps cells by dielectrophoresis force of an electric field. Moreover, in combination with SU-8 microcavities, the cell is captured and held more firmly. Without long-term manipulation under the electric field, the cell viability is increased. This favors the use of the device on cell analysis and research.

2. Compared with the prior art II whose function includes cell analysis and sorting, the present invention also captures and releases cells by dielectrophoresis. However, once the cell is trapped into the microcavity, the electric field of the present invention is immediately turned off. Thus cell damage caused by electric field is avoided and the cell viability is preserved. Thus analysis and study time of cells is increased effectively.

3. The release function of the present invention is base on dielectrophoresis caused by the electric field for releasing cells. There is no need to generate vapor bubbles by increasing or decreasing voltage/frequency for cell release. Because higher or lower voltage/frequency may cause cell death and this has negative effect on the studies.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A chip with tri-layer electrodes and micro-cavity arrays for control of bioparticles comprising:
    an upper layer body, a middle layer body, a lower layer body, and micro flow chambers, wherein the upper layer body, the middle layer body, and the lower layer body are respectively disposed with an electrode and the electrode of the upper layer body and the electrode of the middle layer body are common electrodes while the electrode of the lower layer body is a dispersive electrode array, said electrode on said lower layer body coated with photoresist before being photo exposed to form said micro-cavity arrays;
    said micro-cavity arrays defining a plurality of recesses formed in said middle layer body for releaseably capturing said cells;
    whereby by application of an AC electric field, cell capture, cell release at the single-cell level and cell release at the cell population level are achieved.

2. A manufacturing method for chips with tri-layer electrodes and micro-cavity arrays for control of bioparticles comprising the steps of:
    a) etching a lower-layer electrode in which a glass substrate is coated with a layer of metal by evaporation to form a specimen that is then coated with a photoresist before undergoing a photo exposure; the photo exposed specimen is immersed into a developer for development and is soaked into an etching solution to produce the lower-layer electrode;
    b) constructing microcavities in which the lower-layer electrode of the specimen is coated with photoresist before undergoing a photo exposure; then the photo exposed specimen is immersed into a developer for development and a step of hard bake is performed to complete construction of microcavities;
    c) producing an intermediate structure having a middle-layer electrode in which the microcavities are coated with photoresist before undergoing a photo exposure; then the photo exposed specimen is soaked into a developer for development and is coated with a layer of metal by evaporation; next the photoresist is removed by a lift-off process to produce the middle-layer electrode; and
    d) forming said final chips by covering said intermediate structure with a layer of photoresist before undergoing a photo exposure, developing said photo exposed intermediate structure by covering an upper-layer electrode on respective areas of said developed intermediate structure and connecting said upper-layer electrode to said intermediate structure and said glass substrate to form said final chip for manipulation of cells.

3. The method as claimed in claim 2, wherein the metal coated by evaporation is gold.

4. The method as claimed in claim 2, wherein after completing manufacturing a chip for manipulation of cells, the chip is connected with at least one wire and at least one signal generator so as to be applied to cell manipulation experiments.

* * * * *